United States Patent [19]

Curry et al.

[11] 3,966,087

[45] June 29, 1976

[54] AEROSOL DISPENSING DEVICE CONTAINING A HAIRSETTING PREPARATION HAVING A LOW PROPELLANT CONTENT

[75] Inventors: Kenneth Vasey Curry, Heatherside; Rustom Kooverji Gamadia, London; Barry Graham Pike, Yateley, all of England

[73] Assignee: Lever Brothers Company, New York, N.Y.

[22] Filed: Mar. 29, 1974

[21] Appl. No.: 456,404

[30] Foreign Application Priority Data
Mar. 30, 1973 United Kingdom............... 15323/73

[52] U.S. Cl................................. 222/192; 252/305; 424/DIG. 1; 424/DIG. 2; 424/47; 424/71
[51] Int. Cl.² ............................................ B67D 5/06
[58] Field of Search................. 424/DIG. 1, DIG. 2, 424/47, 70, 71; 252/305; 222/3, 4, 192, 394, 397, 402.1

[56] References Cited
UNITED STATES PATENTS

| | | | |
|---|---|---|---|
| 2,953,498 | 9/1960 | Werner | 424/47 |
| 3,131,152 | 4/1964 | Klausner | 424/70 X |
| 3,405,084 | 10/1968 | Bohac et al. | 424/47 X |
| 3,460,714 | 8/1969 | Mace | 222/4 |
| 3,555,145 | 1/1971 | Wetzel et al. | 424/47 |
| 3,577,517 | 5/1971 | Kubot et al. | 424/47 |
| 3,606,963 | 9/1971 | Marand | 222/132 |
| 3,624,793 | 11/1971 | Marand | 222/95 |
| 3,658,215 | 4/1972 | Ewald | 222/402.18 |
| 3,715,428 | 2/1973 | Quasius et al. | 424/47 |
| 3,790,664 | 2/1974 | Krochock et al. | 424/47 |

*Primary Examiner*—Albert T. Meyers
*Assistant Examiner*—Vera C. Clarke
*Attorney, Agent, or Firm*—Kenneth F. Dusyn; James J. Farrell; Melvin H. Kurtz

[57] ABSTRACT

An aerosol hairsetting preparation comprises a film-forming resin and a minor amount of a propellant dissolved in water and optionally a water-miscible organic solvent. The product is preferably dispensed from an aerosol can having two compartments connected by a gas valve, one compartment containing the product and the other containing propellant gas.

2 Claims, No Drawings

3,966,087

AEROSOL DISPENSING DEVICE CONTAINING A HAIRSETTING PREPARATION HAVING A LOW PROPELLANT CONTENT

The invention relates to hairsetting preparations which are dispensed as a single liquid phase from a pressurized pack, such as an aerosol device.

Hair preparations normally contain a high proportion, usually at least 50% by weight, of liquefied gas propellant in order to ensure, in the interests of economy, that substantially all the contents of the pack are dispensed before the propellant is exhausted. There are, however, drawbacks with preparations of this type. For example, it can be disadvantageous to dispense a high proportion of propellant with the preparation, since this can cause an unpleasant cooling sensation on the skin or it can, in the case of a hairspray, lead to an increase in viscosity of the dispensed preparation as propellant is lost, thereby restricting spreading of the atomized preparation on the hair. Also preparations which include a substantial proportion of water tend to produce a two liquid phase system in the presence of a high proportion of propellant, and it is then necessary to shake the pressurized pack immediately before each use in order to ensure that the preparation is correctly dispensed. Even then, some liquid phase separation may occur while the preparation is actually being dispensed; this can lead to preferential depletion of preparation or propellant resulting in a variable and continuously declining performance of the preparation.

We have now devised a hairsetting preparation which is characterized by a low propellant content and which is dispensed from a pressurized pack as a single liquid phase by propellant gas at substantially constant pressure.

Accordingly, the invention provides a single liquid phase hairsetting preparation comprising by weight from 50 to 99% water and from 0 to 40% of a water-miscible organic solvent, together with from 0.2 to 5% of a film-forming resin and up to 25% of a propellant dissolved therein.

The invention also provides an aerosol device for dispensing the single liquid phase hair setting preparation.

The amount of propellant dissolved in the preparation forms no more than 25%, usually from 0.001 to 20% and preferably 5 to 15% by weight of the preparation.

The propellant can be either a liquefiable gas or a mixture of a permanent gas and a liquefiable gas.

Examples of suitable liquefiable gaseous propellants are halocarbons such as propellant 12 (dichlorodifluoromethane) or blends of propellant 12 with propellant 11 (trichlorofluoromethane), propellant 114 (symmetrical dichlorotetrafluoroethane) and propellant 22 (chlorodifluoromethane), such as 11/12; 11/12/114; 11/12/22; 12/114; 22/114; 12/22/114; and hydrocarbon propellants such as butane, isobutane, propane, pentane or isopentane or certain mixtures thereof.

Examples of suitable permanent gases are carbon dioxide, nitrogen and nitrous oxide.

The proportion of water in the preparation forms from 50–99%, preferably 60–80% by weight and the proportion of water-miscible organic solvent is from 0–40%, preferably 10–30% by weight. The organic solvent, if present, is usually ethanol or isopropanol or other water-miscible low boiling solvents or mixtures thereof.

It is an important feature of the invention that water, organic solvent, if present, and dissolved propellant together form a single liquid phase in which the film-forming resin is in solution.

The proportion of film-forming resin can form from about 0.2–5%, preferably 1–4% by weight of the total preparation.

Any of the usual film-forming resins which are used in hair preparations can be used, provided of course that they are soluble in the single liquid phase which characterizes the preparation.

Examples of such resins are:

LUVISKOL VA 28I (available from BASF) — a copolymer containing 20% vinyl pyrrolidone and 80% vinyl acetate (supplied as a 50% solution in isopropanol), and having a K value (as determined in the Ubbelohde viscometer — No 1 capillary — in 1% ethanolic solution) of 16 ± 5.

LUVISKOL VA 37E (available from BASF) — a copolymer containing 30% vinyl pyrrolidone and 70% vinyl acetate (supplied as a 50% solution in ethanol), and having a K value (as determined in the Ubbelohde viscometer — No 1 capillary — in 1% ethanolic solution) of 34 ± 3.

BINA 405 (available from G Barr Railroad Co) — an acrylic ester amide copolymer containing carboxyl groups.

[NATIONAL STARCH] RESYN 28-1310 (available from National Starch and Chemical Corporation) — a copolymer of vinyl acetate and crotonic acid having in intrinsic viscosity as measured in acetone at 30°C of 0.3.

ARISTOFLEX C (available from Hoechst Chemical Division) — a copolymer of vinyl acetate and crotonic acid, having a Hoeppler viscosity as measured at 20°C as a 20% solution in 96% ethanol of 20 –35 cP.

VEM 640-M48 (manufactured by Dutton & Reinish Ltd) — a vinyl terpolymer containing ester, acrylic and carboxylic groups (supplied as a 50% solution in ethanol) and having a viscosity at 25°C using the Brookfield Viscometer, No. 3, Disc, of 4000–6000 cP.

GANTREZ ES 225 (available from GAF Corporation) — a copolymer of methyl vinyl ether and monoethyl ester of maleic acid (supplied as a 50% solution in ethanol).

GANTREZ ES 335-1 (available from GAF Corporation) — a copolymer of methyl vinyl ether and monoisopropyl ester of maleic acid (supplied as a 50% solution in isopropanol).

GANTREZ ES 435 (available from GAF Corporation) — a copolymer of methyl vinyl ether and monobutyl ester of maleic acid (supplied as a 50% solution in isopropanol).

GAFQUAT 734 and 755 (available from the GAF Corporation) — quaternised vinyl pyrrolidone copolymers having an average molecular weight of <100,000 and >1,000,000 and a relative viscosity (Ostwald-Fenske) of 2.5 to 3.5 and 1.5 to 2.0 (1% in alcohol) respectively.

POLYCUP 171 (available from the Hercules Chemical Company) — a polyamide epichlorhydrin condensate (supplied as a 10% solution in water).

PVP [PVP] K30 (available from BASF) — a polymer of vinyl pyrrolidone having a molecular weight of approx. 40,000 and a K value (as determined in the Ubbelohde viscometer - No 1 capillary — in 1% aqueous solution) of 30 ± 3.

The hair setting preparation can optionally contain other additives well known in the art to improve the performance and properties of this type of product. For example, alternative solvents such as methylene chloride can be used to vary the dispersibility of the product when it is discharged. Also, solvents or plasticizers such as for example ethylene glycol monomethyl ether, ethylene glycol monoethyl ether, ethylene glycol, diethylene glycol, polyethylene glycol, hexylene glycol, glycerol monoacetate, diacetate or triacetate, oleyl alcohol, triethyl phosphate, dimethyl phthalate, diethyl phthalate, dibutyl phthalate, glycerol monoricinoleate, isopropyl lanolate, lanolin and lanolin derivatives, dimethyl polysiloxane and methylphenylpolysiloxane.

It is also possible to include other additives which are customary in cosmetics, for example perfumes, dyestuffs, glossing agents such as silicones, conditioning agents such as proteins, cationic products to facilitate disentangling, nonionic products to provide peptization of the perfumes, urea to facilitate penetration into the hair fibre and anti-seborrhoeic products.

The invention is particularly adapted for use in a pressurized pack of the type disclosed in our British Pat. No. 1,390,937. It will be appreciated, however, that other pressurized packs incorporating at least two compartments having a gas communication means between a propellant reservoir compartment and a preparation compartment can be employed for dispensing the hairsetting preparations herein defined. Accordingly, it is not intended that the present invention is to be limited solely to the use of a pressurized pack of the type covered by the aforementioned patent.

According to one embodiment of the invention, there is provided an aerosol dispensing device having a first compartment containing the single liquid phase hairsetting preparation as herein defined and a second compartment containing a reservoir of propellant gas together with liquefied gaseous propellant; and a communicating means, such as a valve, adapted to communicate the second compartment with the first compartment, thereby to allow propellant gas to pass from the second compartment to the first compartment following a momentary fall in pressure in the first compartment on dispensing the product.

When packaging preparations according to the invention, it is convenient according to a preferred technique to fill the upper compartment of a two compartment pack of the type described in our British Pat. No. 1,390,937 with the preparation comprising water or water/solvent solution of the resin but without liquefied propellant. The lower compartment which forms a reservoir is then filled with sufficient propellant to enable all of the preparation eventually to be dispensed. During a period of equilibration after filling, some propellant gas passes via the valve to the upper compartment to fill the headspace with propellant gas, some of which will dissolve in the preparation.

It is of course also possible when filling a pressurized pack of this type to include some liquefied propellant with the preparation in the upper compartment.

In use, the preparation which will also usually include at least a little of the propellant dissolved in it is dispensed from the upper compartment via the usual spray valve, whereupon propellant gas passes from the reservoir to replenish and maintain the constant pressure in the upper compartment.

The hairsetting preparation according to the invention is preferably applied to the hair before it has been styled and usually when it is in a wet condition, for example after washing. The hair is then set in a desired configuration and dried.

The invention is illustrated by the following Examples.

EXAMPLE 1

A hairsetting aid concentrate was prepared by mixing the following ingredients:

|  | % w/w |
| --- | --- |
| LUVISKOL VA 37E | 4 |
| Industrial Methylated Spirit | 25 |
| Water | 71 |

140 g of this concentrate were then filled into the upper compartment (capacity 230 ml) of a two compartment pack of the type described in our British Pat. No. 1,390,937.

The lower compartment (capacity 50 ml) of the pack was filled with 25 g of a blend of 20 parts by weight of propellant 114 and 80 parts of propellant 12.

During a period of equilibration, propellant gas entered the upper compartment, pressurized the headspace and dissolved in the concentrate to an extent of about 1% by weight.

EXAMPLE 2

Example 1 was repeated using the following concentrate ingredients:

|  | % w/w |
| --- | --- |
| Film-forming resin - PVP K30 | 2 |
| Water | 98 |

The same propellant blend was used, the amount of propellant dissolving in the concentrate was about 0.02% by weight.

EXAMPLE 3

Example 1 was repeated using the following concentrate ingredients:

|  | % w/w |
| --- | --- |
| National Starch Resyn 28-1310 | 1.8 |
| 2-amino-2-methyl propan-1-ol | 0.15 |
| Industrial methylated spirit | 30.0 |
| Water | 68.05 |

The same propellant blend was used, the amount of propellant dissolving in the concentrate was about 1% by weight.

What is claimed is:
1. An aerosol dispensing device having
   i. a first compartment containing a single liquid phase product and propellant in gaseous form, said single liquid phase comprising by weight from about 50 to about 99% water, from 0 to about 40% of a water-miscible organic solvent, from about 0.2 to about 5% of a film-forming resin and from about 0.001 to about 25% of a propellant dissolved therein;
   ii. a dispensing valve arranged to interconnect the first compartment and the atmosphere;

iii. a second compartment containing propellant gas; and
iv. a communicating valve arranged to interconnect the second compartment and the first compartment, thereby to allow the propellant gas to pass from the second compartment to the first compartment.

2. The aerosol dispensing device according to claim 1, wherein in the second compartment the propellant gas is a mixture of a permanent gas and a liquified gaseous propellant.

* * * * *